(12) United States Patent
Filippi et al.

(10) Patent No.: US 7,727,482 B2
(45) Date of Patent: Jun. 1, 2010

(54) METHOD FOR CARRYING OUT CHEMICAL REACTIONS IN PSEUDO-ISOTHERMAL CONDITIONS

(75) Inventors: Ermanno Filippi, Castagnola (CH); Enrico Rizzi, Casnate con Bernate (IT); Mirco Tarozzo, Ligornetto (CH)

(73) Assignee: Methanol Casale S.A. (CH)

( * ) Notice: Subject to any disclaimer, the term of this patent is extended or adjusted under 35 U.S.C. 154(b) by 525 days.

(21) Appl. No.: 10/541,432

(22) PCT Filed: Jan. 15, 2004

(86) PCT No.: PCT/EP2004/000233

§ 371 (c)(1), (2), (4) Date: Jul. 5, 2005

(87) PCT Pub. No.: WO2004/071650

PCT Pub. Date: Aug. 26, 2004

(65) Prior Publication Data

US 2006/0171859 A1 Aug. 3, 2006

(30) Foreign Application Priority Data

Feb. 17, 2003 (EP) .................................. 03003573

(51) Int. Cl.
*G05D 23/00* (2006.01)

(52) U.S. Cl. .................. 422/109; 422/110; 422/198; 422/200; 422/201; 208/134

(58) Field of Classification Search .................. 422/198, 422/199, 109, 110, 200, 201; 208/134; 165/104.11, 165/104.19; 73/204.3
See application file for complete search history.

(56) References Cited

U.S. PATENT DOCUMENTS

| 4,488,239 | A |   | 12/1984 | Agarwal |
| 5,600,053 | A | * | 2/1997 | Girod et al. .................. 585/654 |
| 6,608,234 | B2 | * | 8/2003 | Saruwatari .................. 568/728 |
| 6,759,562 | B2 | * | 7/2004 | Gartside et al. ............. 585/265 |
| 7,033,553 | B2 | * | 4/2006 | Johnston et al. ............. 422/199 |
| 7,645,428 | B2 | * | 1/2010 | Arencibia, Jr. .............. 422/202 |

FOREIGN PATENT DOCUMENTS

| EP | 0 094 208 A2 |   | 11/1983 |
| EP | 1 060 788 | * | 12/2000 |
| EP | 1 153 653 | * | 11/2001 |
| FR | 2 256 778 A |   | 8/1975 |
| GB | 758 538 |   | 10/1956 |
| GB | 1088009 A |   | 10/1967 |
| JP | 59 039342 A |   | 3/1984 |

* cited by examiner

*Primary Examiner*—N. Bhat
(74) *Attorney, Agent, or Firm*—Akerman Senterfitt

(57) ABSTRACT

Method for controlling the reaction temperature in a catalytic bed (24) of a reactor (1) in which a chemical reaction takes place in pseudo-isothermal conditions by means of at least one heat exchanger (12), crossed by a respective operating fluid, immersed in the catalytic bed (24).

4 Claims, 3 Drawing Sheets

METHOD FOR CARRYING OUT CHEMICAL REACTIONS IN PSEUDO-ISOTHERMAL CONDITIONS

FIELD OF APPLICATION

In its most general aspect the present invention refers to a method for carrying out chemical reactions in controlled pseudo-isothermal conditions, in other words in conditions in which the reaction temperature is kept in a tight range of values about a predetermined reaction temperature T.

In particular, the present invention regards a method for controlling the reaction temperature in a catalytic bed of a reactor in which a chemical reaction takes place in pseudo-isothermal conditions through at least one heat exchanger, crossed by a respective operating fluid, immersed in said catalytic bed.

PRIOR ART

It is known, for pseudo-isothermal reactions and catalytic reactors of the prior art, to control the reaction temperature through heat exchange between the operating fluid, which flows inside suitable heat exchangers, and the catalytic bed in which said exchangers are immersed and in which the reaction takes place.

And it is known that an optimization of such an exchange is constantly sought after, in order to improve the yield of the reaction. This exchange is carried out so as to allow the transfer of the largest possible amount of heat between operating fluid and catalytic bed, that is, maximizing the heat exchange coefficient inside the heat exchangers, where the operating fluid flows, and inside the catalytic bed.

By doing so, however, it has been noticed that temperature gradients even of a significant value take place in the catalytic bed.

In particular, the temperature in each point of the bed varies between a first value at the heat exchangers, i.e. at the temperature of the outer wall of the exchangers themselves, and a second temperature value detected in those points of the catalytic bed situated at the maximum distance from the heat exchangers.

In the rest of the description and in the subsequent claims, said second temperature value shall be identified with the term "limit temperature" $T_1$.

If the reaction taking place inside the reactor is exothermic, said limit temperature $T_1$, shall correspond to a predetermined maximum value $T_{max}$ of the temperature, above which it is not convenient to make the reaction take place, since secondary reactions intervene which decrease the yield and, moreover, a decrease in efficiency of the catalyst takes place.

If the reaction taking place inside the reactor is endothermic, said limit. temperature $T_1$ shall correspond to a temperature value, below which the reaction does not take place.

The consequent dishomogeneity in the distribution of the temperature leads far, inside of the catalytic bed, from the desired pseudo-isothermal conditions, with a worsening of the global yield of the reactor itself.

SUMMARY OF THE INVENTION

The technical problem underlying the present invention is that of realizing a method for controlling, in a simple manner, the pseudo-isothermicity of a chemical reaction inside a catalytic bed by reducing the temperature difference ($\Delta T$) between the temperature of the catalytic bed at the walls of the heat exchangers and the limit temperature $T_1$, or, in other words, by reducing the size of the temperature gradient between the outer wall of the exchanger and the limit temperature $T_1$.

In such a way the drawbacks of the prior art are overcome.

The aforementioned technical problem is solved according to the invention by a method for controlling the reaction temperature in a catalytic bed of a reactor in which a chemical reaction takes place in pseudo-isothermal conditions by means of at least one heat exchanger, crossed by a respective operating fluid, immersed in said catalytic bed, which method is characterized in that it comprises the step of:

setting the speed of said heat exchange fluid inside the respective heat exchanger within predetermined values, so that the heat exchange coefficient inside said heat exchanger is less than the heat exchange coefficient in the catalytic bed.

By reducing the heat exchange coefficient inside the heat exchanger below that inside the catalytic bed, an increase in the temperature gradient inside said exchanger is obtained and the temperature at the wall of the heat exchanger is consequently increased.

The end result is the decrease in the aforementioned temperature difference $\Delta T$ between the temperature of the catalytic bed at the wall of a heat exchanger and the limit temperature $T_1$, in the catalytic bed.

In stark contrast with the constant teaching of the prior art, it has been surprisingly seen that, by suitably reducing the heat exchange coefficient inside the heat exchangers, the reactant/product mixture that crosses the catalytic bed benefits from greater uniformity of temperature (lower $\Delta T$) which in turn allows to obtain a greater efficiency of reaction and thus greater global conversion yield.

Preferably, but not for limiting purposes, the speed of said heat exchange fluid inside the respective heat exchanger is regulated within values such that the heat exchange coefficient inside the heat exchangers is equal to or less than ⅔ the heat exchange coefficient inside the catalytic bed.

Said method allows the technical problem to be solved and the drawbacks of the prior art as described above to be overcome.

According to one particular aspect of the present invention the heat exchangers immersed in the catalytic bed are at least two in number and the method just described is characterized in that it comprises the steps of:

continuously detecting in said catalytic bed the temperature difference $\Delta T$ between the temperature of the catalytic bed at said heat exchangers and a limit temperature $T_1$, at a middle point between said heat. exchangers;

varying the speed of said heat exchange fluid inside said heat exchangers, according to the aforementioned temperature difference $\Delta T$, obtaining a corresponding variation of the heat exchange coefficient inside said heat exchangers.

Further characteristics and advantages of the invention will become clearer from the detailed description of an embodiment of a method according to the invention, given hereafter with reference to the attached drawings, for indicative and non-limiting purposes.

DETAILED DESCRIPTION OF A PREFERRED EMBODIMENT OF THE INVENTION

Figure 1:
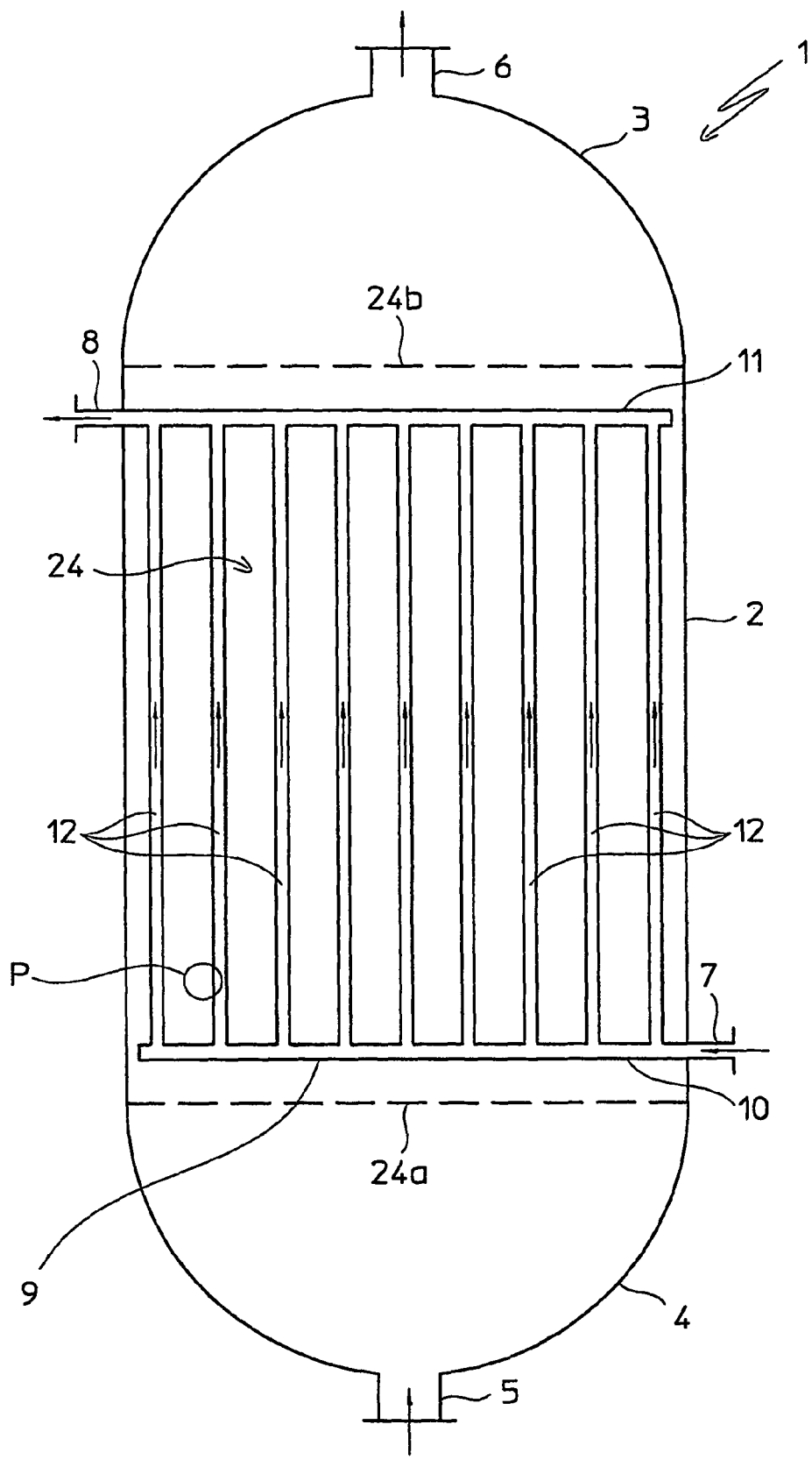
FIG. 1 schematically shows a section view of a pseudo-isothermal reactor for carrying out the method of the present invention.

With reference to FIG. 1, a catalytic pseudo-isothermal chemical reactor for the synthesis of chemical substances such as ammonia, methanol, formaldehyde and nitric acid, according to the method of the present invention is generally indicated with 1.

Said reactor 1 comprises a cylindrical shell 2, an upper base plate 3 and a lower base plate 4, an opening 5 for feeding the reactants, an opening 6 for discharging the reaction products, an opening 7 for feeding an operating heat exchange fluid and an opening 8 for discharging said operating fluid.

The reactor 1 also comprises a catalytic bed 24, defined between the broken lines 24a and 24b and supported in a per se known way, inside of which a heat exchange unit 9 is placed, which in turn comprises a plurality of heat exchangers 12. The heat exchangers 12 are in fluid communication with said feed opening 7, at a lower end thereof, through a distributor duct 10, and in fluid communication with said discharge opening 8, at an opposite end, through a collector duct 11. In particular, said heat exchangers 12 are for example heat exchange tubes or plates.

Figure 2:
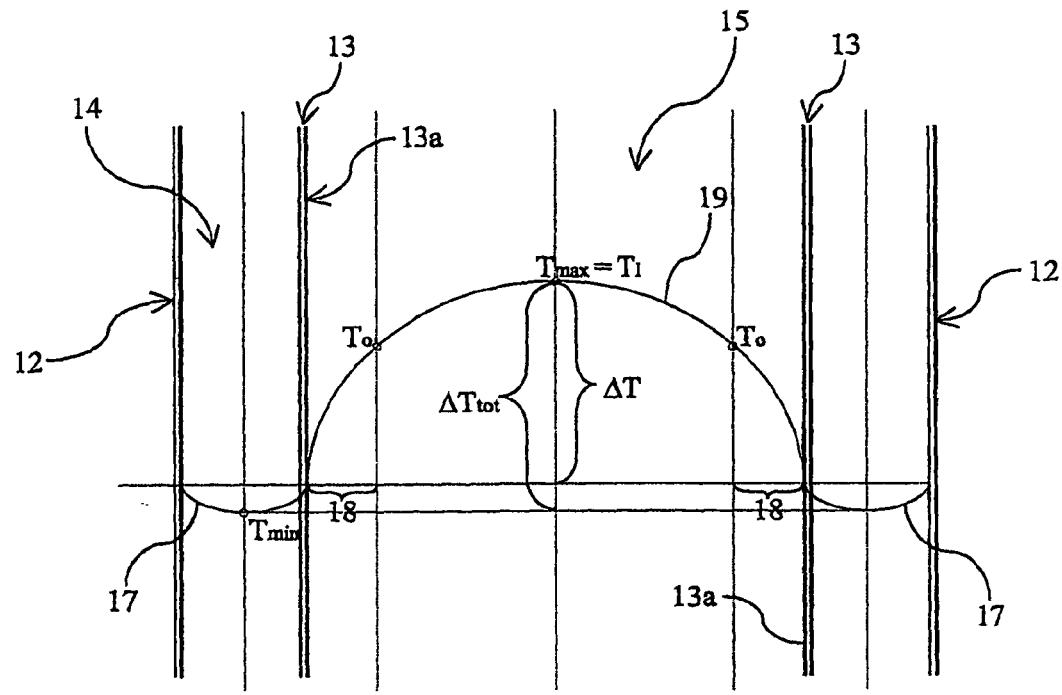
FIG. 2 schematically shows a pseudo-isothermal reactor operating according to the method of the prior art and relative temperature profile.
Figure 3:
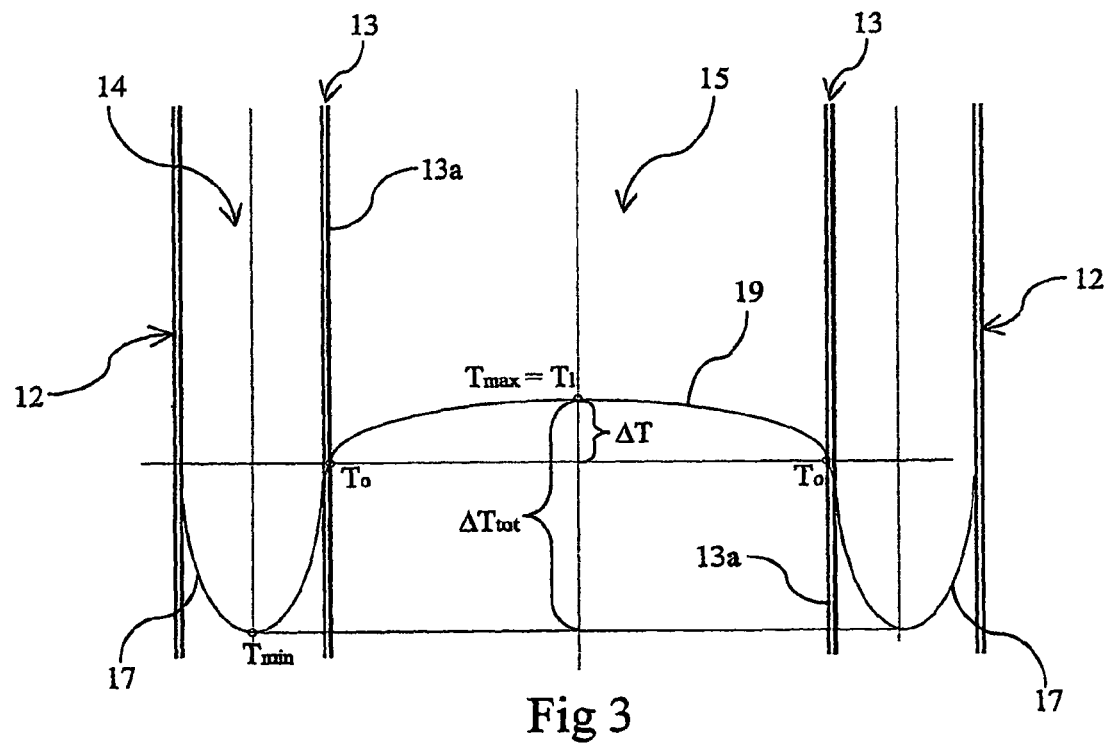
FIG. 3 schematically shows a section view of a detail of the pseudo-isothermal reactor of FIG. 1 and relative temperature profile.

FIGS. 2 and 3 represent a detail of a pseudo-isothermal reactor operating according to the method of the prior art and a detail of the reactor of FIG. 1 operating according to the method of the present invention, respectively.

In such figures, details that are equivalent to each other and/or equivalent to the details of the reactor of FIG. 1, are indicated with the same reference numerals.

With 13 is generally indicated the wall of the heat exchangers 12 situated inside the catalytic bed 24. With 13a, on the other hand, we wish to indicate the outer surface or catalyst-side surface of the wall 13 of the heat exchangers 12.

In operation, the heat exchange operating fluid crosses a zone 14, inside the heat exchangers 12, whereas the mixture of reactants and products flows in a reaction zone 15 of the catalytic bed 24 defined between adjacent heat exchangers 12.

The profile of the distribution of the temperatures is represented in both FIGS. 2 and 3 by lines 17 and 19. Line 17 is relative to the distribution of temperatures in the zone 14, inside the exchangers 12, whereas line 19 is relative to the distribution of the temperatures in the zone 15, inside the catalytic bed 24. In general, the profile of the temperatures inside the respective pseudo-isothermal reactor is that resulting from the combination of lines 17 and 19.

In the reactors of the prior art (FIG. 2), it can be easily noted how the lines 17 are very flat, almost rectilinear and perpendicular to the wall 13 of the heat exchangers 12. This is determined by a high heat exchange coefficient (the highest possible) inside such heat exchangers 12.

Differently, still in reactors of the prior art (FIG. 2), the line 19 relative to the distribution of the temperatures in the zone 15 of the catalytic bed 24 has a substantial arc. This is caused, on the one hand, by the different (lower) heat exchange coefficient present in the catalytic bed 24 with respect to the heat exchange coefficient (greater) inside the exchangers 12, which causes a great temperature difference (dishomogeneity) between the wall temperature (surface 13a) of the exchangers 12 and the temperature of the reactant/product mixture flowing in the reaction zone 15.

In other words, the temperature varies, between two zones 14 and 15, between a minimum value $T_{min}$ corresponding to the centre of the zone 14 inside the heat exchangers 12 and a maximum value $T_{max}$ (equivalent to the limit temperature $T_1$ described above) corresponding to the centre of the zone 15 of the catalytic bed 24 (i.e. in the middle point between two adjacent heat exchangers 12).

Between the two zones 14 and 15 there is therefore a temperature gradient $\Delta T_{tot}$, which, as can be seen in FIG. 2, is situated mainly in zone 15, creating a high dishomogeneity of temperature in the catalytic bed 24, with a consequent loss in reaction efficiency and thus reduction in the conversion yield, for the reasons described hereafter.

The part of the temperature gradient $\Delta T_{tot}$ situated in zone 15 is represented with reference symbol $\Delta T$, which stands to indicate the temperature difference, described above, between the limit temperature $T_1$, (corresponding to $T_{max}$) and the temperature at the outer surface 13a of the exchangers 12.

Inside the temperature difference (or gradient) $\Delta T$, in the reaction zone 15, a temperature range is identified where the reaction takes place in efficient conditions, and thus with optimal yield (pseudo-isothermal conditions). Such a temperature range is between temperature $T_{max}$ ($=T_1$) and a temperature $T_0$ below which the reaction does not take place or at least takes place in inefficient conditions.

From FIG. 2, it is clear how in a considerable portion of zone 15 of the catalytic bed 24, identified with 18, the reaction temperature is below the optimal values to the detriment of the efficiency and global conversion yield of the reactor.

Thanks to the method according to the present invention, by suitably adjusting the crossing speed of said heat exchanger 12, by the operating fluid (i.e. in the case of the example of FIG. 3, reducing such a speed with respect to the crossing speed of the example of FIG. 2) the heat exchange coefficient inside the heat exchangers 12 is advantageously reduced to lower values with respect to the heat exchange coefficient inside the catalytic bed 24.

In this way, as represented in FIG. 3, an increase in the temperature gradient inside the exchangers 12 is obtained (line 17 indeed has greater concavity with respect to FIG. 2) and the temperature is consequently increased at their outer surface 13a. Consequently, with the same temperature gradient $\Delta T_{tot}$ between zones 14 and 15 with respect to the prior art (FIG. 2), the temperature gradient in zone 15 of the catalytic bed 24 is reduced, i.e. the temperature difference $\Delta T$ between the limit temperature $T_1$ (corresponding to $T_{max}$) and the temperature at the outer surface 13a of the exchangers 12 is reduced.

For this reason, the profile of the temperatures (line 19) in said zone 15 has a very small concavity and, as indicated in FIG. 3, is within the temperature range ($T_{max}$-$T_0$) where the reaction takes place in optimal efficiency (and thus yield) conditions (pseudo-isothermal conditions).

For this reason, in whole zone 15 of the catalytic bed 24 it is possible to carry out the reaction efficiently to the great advantage of the global conversion yield.

According to a particular and advantageous aspect of the present invention, the temperature difference $\Delta T$ between the limit temperature $T_1$, (corresponding to $T_{max}$) and the temperature at the outer surface 13a of the exchangers 12 is detected continuously, and the speed of the heat exchange fluid flowing inside the heat exchangers 12 is varied according to the aforementioned temperature difference $\Delta T$, obtaining a corresponding variation in the heat exchange coefficient inside said heat exchangers 12 and thus of the temperature difference (gradient) ΔT inside zone 15 of the catalytic bed 24.

Figure 4:
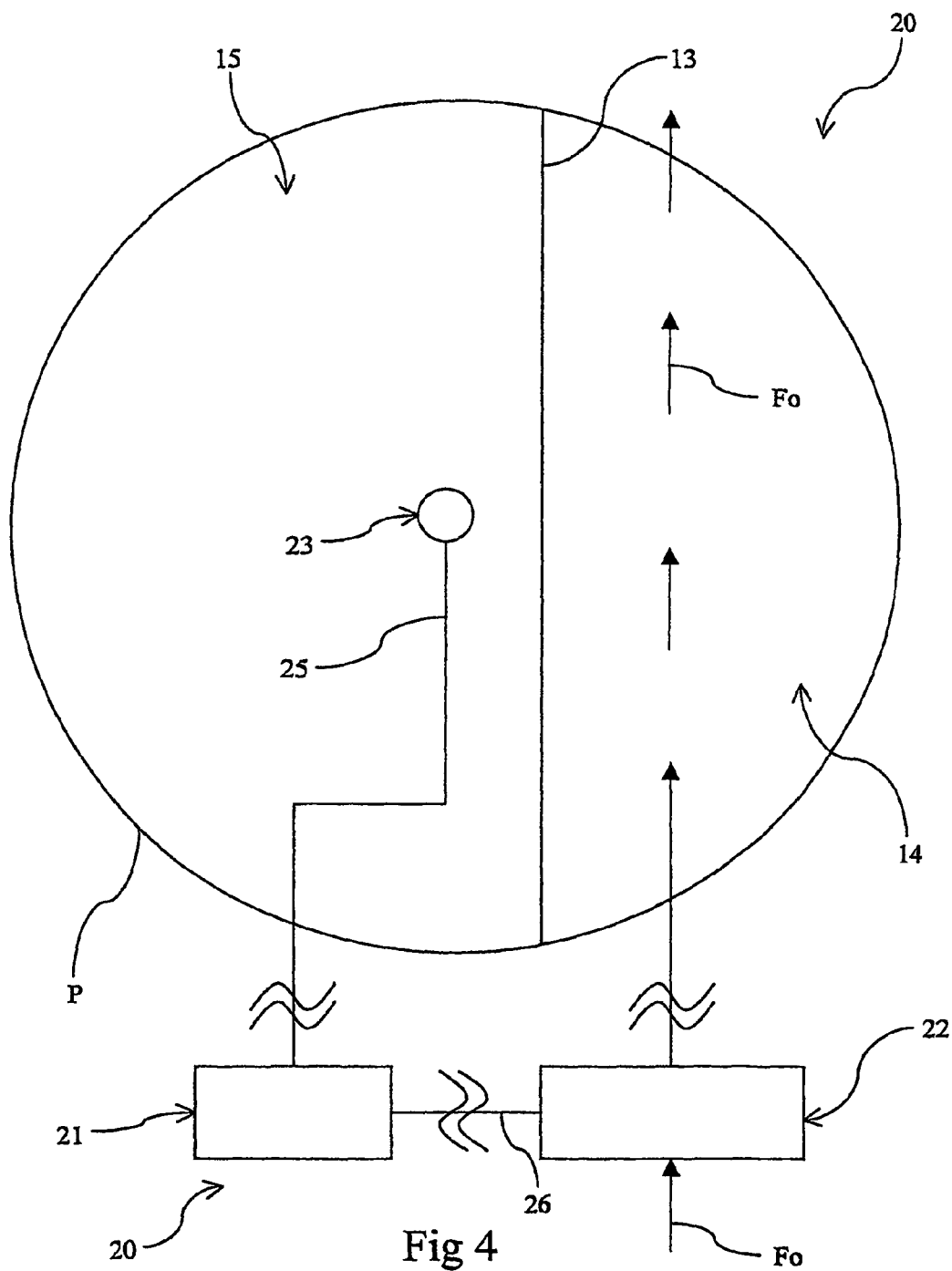
FIG. 4 schematically shows an enlarged section view of a further detail of the pseudo-isothermal reactor of figure 1.

For such a purpose the pseudo-isothermal reactor of FIG. 1 comprises an apparatus 20, represented schematically in FIG. 4, for continuously detecting the temperature in zone 15 of the catalytic bed 24 and the variation—still continuously—of the speed of the operating fluid flowing inside the heat exchangers 12 according to the temperature detected.

In such a figure, details equivalent to the details of the previous figures are indicated with the same reference symbols.

The apparatus 20 (FIG. 4) comprises at least one probe 23 (for example a thermocouple) situated inside the reaction zone 15, for continuously measuring the temperature difference ΔT between the temperature in the centre of zone 15 and the temperature at the outer surface 13a of the heat exchangers 12.

Such an apparatus 20 also comprises a control unit 21, in data communication—through the flowline 25—with the probe 23, which processes the temperature values detected by the probe 23, and a feeding speed regulator 22 of the operating fluid $F_o$ to the heat exchangers 12, controlled by said control unit 21 (flowline 26). This regulator 22 can, for example, be a valve or a pump for feeding operating fluid.

The reference symbol P stands to indicate a detail inside the reactor 1 of FIG. 1, represented enlarged in FIG. 4 to better highlight the characteristics of the apparatus 20.

This solution allows the temperature difference ΔT inside reaction zone 15 to be constantly controlled, dynamically calibrating the delivery speed of operating fluid $F_o$ inside the heat exchangers 12.

The invention thus conceived is susceptible to further variants and modifications all of which are within the capabilities of the man skilled in the art and, as such, fall within the scope of protection of the invention itself, as defined by the following claims.

The invention claimed is:

1. A method for controlling the reaction temperature in a catalytic bed of a reactor in which a chemical reaction takes place in pseudo-isothermal conditions by means of at least one heat exchanger, crossed by a respective operating fluid immersed in said catalytic bed, comprising the step of:
    setting the velocity of said heat exchange fluid inside the respective heat exchanger within predetermined values, so that the heat transfer coefficient inside said heat exchanger is less than the heat transfer coefficient in the catalytic bed.

2. The method according to claim 1, wherein said velocity of said heat exchange fluid inside the respective heat exchanger is regulated within values such that the heat transfer coefficient inside the heat exchangers is equal to or less than ⅔ the heat transfer coefficient inside the catalytic bed.

3. The method according to claim 1, wherein said reactor comprises at least two heat exchangers immersed in the catalytic bed and wherein the method further comprises the steps of:
    continuously detecting in said catalytic bed the temperature difference ΔT between the temperature of the catalytic bed at said heat exchangers and a limit temperature $T_1$, at a middle point between said heat exchangers; and
    varying the velocity of said heat exchange fluid inside said heat exchangers, according to the aforementioned temperature difference ΔT, obtaining a corresponding variation of the heat transfer coefficient inside said heat exchangers.

4. A pseudo-isothermal chemical reactor comprising:
    a catalytic bed;
    at least two heat exchangers immersed in said catalytic bed; and
    an apparatus for adjusting the temperature inside a reaction zone of said catalytic bed defined between said heat exchangers, comprising
        a probe for continuously measuring the temperature difference ΔT between the temperature in a central position of said zone and the temperature of said reaction zone at said heat exchangers,
        a control unit, in data communication with said probe, and
        a feeding velocity regulator for an operating fluid ($F_o$) in said heat exchangers, in data communication with said control unit.

* * * * *